(12) United States Patent
Hsu et al.

(10) Patent No.: US 8,114,834 B2
(45) Date of Patent: Feb. 14, 2012

(54) SELF-ASSEMBLING PEPTIDE AMPHIPHILES

(75) Inventors: Lorraine Hsu, Chicago, IL (US); Samuel I. Stupp, Chicago, IL (US)

(73) Assignee: Northwestern University, Evanston, IL (US)

( * ) Notice: Subject to any disclaimer, the term of this patent is extended or adjusted under 35 U.S.C. 154(b) by 197 days.

(21) Appl. No.: 11/936,927

(22) Filed: Nov. 8, 2007

(65) Prior Publication Data

US 2008/0175883 A1 Jul. 24, 2008

Related U.S. Application Data

(60) Provisional application No. 60/857,931, filed on Nov. 9, 2006.

(51) Int. Cl.
*A61K 38/00* (2006.01)
*A61P 31/04* (2006.01)
*A61P 43/00* (2006.01)

(52) U.S. Cl. ........................ 514/3.2; 514/16.5

(58) Field of Classification Search ........................ None
See application file for complete search history.

(56) References Cited

U.S. PATENT DOCUMENTS

| | | | | |
|---|---|---|---|---|
| 5,512,294 | A * | 4/1996 | Li et al. | 424/450 |
| 6,096,863 | A | 8/2000 | Fields | |
| 6,306,598 | B1 | 10/2001 | Charych | |
| 6,875,744 | B2 * | 4/2005 | Owen | 514/16 |
| 6,890,654 | B2 * | 5/2005 | Stupp et al. | 428/403 |
| 7,030,167 | B2 | 4/2006 | Gunther | |
| 7,371,719 | B2 | 5/2008 | Stupp | |
| 2008/0248569 | A1 * | 10/2008 | Mata et al. | 435/375 |

OTHER PUBLICATIONS

Hartgerink et al. Peptide-amphiphile nanofibers: A versatile scaffold for the preparation of self-assembling materials. PNAS. Apr. 16, 2002, vol. 99, No. 8, pp. 5133-5138.*
Reichel et al. Synthesis and Supramolecular Characterization of a Novel Class of Glycopyranosyl-Containing Amphiphiles. J Org Chem. 2000, vol. 65, pp. 3357-3366.*
Biesalski et al. Polymerized Vesicles Containing Molecular Recognition Sites. Langmuir. 2005. vol. 21, pp. 5663-5666.*
Gill et al. Solid-State Sol-Gel Biosensors. Angew. Chem, 2003, vol. 115, pp. 3386-3389.*
Beniash et al., "Self-assembling peptide amphiphile nanofiber matrices for cell entrapment." 2005, Acta Bio. 1:387-397.
Biesalski et al., "Cell adhesion on a polymerized peptide-amphiphile monolayer." 2006, Biomaterials 27:1259-1269.
Biesalski et al. "Polymerized vesicles containing molecular recognition sites" 2005, Langmuir 21:5663-6.
Bull et al., "Self-assembled peptide amphiphile nanofibers conjugated to MRI contrast agents" 2005, Nano Lett. 5:1-4.
Cai et al., "Fabrication of Extended Conjugation Length Polymers within Diacetylene Monolayers on Au Surfaces: Influence of UV Exposure Time," Langmuir 1999, 15, 1215-1222.
Chothia et al., "Conformation of twisted beta-pleated sheets in proteins" Journal of Molecular Biology 1973, 75:295-302.
Hartgerink et al., "Peptide-Amphiphile Nanofibers: A Versatile Scaffold for the Preparation of Self-Assembling Materials." PNAS 2002 vol. 99 No. 8 pp. 5133-5138.
Huo et al., "Unusual chromatic properties observed from polymerized dipeptide diacetylenes," Chemical Communications 1999, 1601-1602.
Jahnke et al., "Topochemical polymerization in supramolecular polymers of oligopeptide-functionalized diacetylenes" 2006, Angew. Chem. 45:5383-5386.
Kolusheva et al., "Color fingerprinting of proteins by calixarenes embedded in lipid/polydiacetylene vesicles" 2006, J. Am. Chem. Soc. 128:13592-98.
Lee et al., "Surface dispersion and hardening of self-assembled diacetylene nanotubes" 2005, Nano Lett. 5:2202-6.
Mori et al., "Parallel Beta-sheet as a Novel Template for Polymerization of Diacetylene," Chemistry Letters 2005, 34, 116-117.
Nezu and Lando, "Polymerization and Characterization of Polyfunctional Ampilphilic Diacetlynes" 1995, 33:2455.
Niece et al., "Self-assembly combining two bioactive peptide-amphiphile molecules into nanofibers by electrostatic attraction" 2003, J. Am. Chem. Soc. 125:7146-47.
Okada et al., "Color and Chromism of Polydiacetylene Vesicles," Accounts of Chemical Research 1998, 31:229-239.
Paramonov et al., "Self-assembly of peptide-amphiphile nanofibers: the roles of hydrogen bonding and amphiphilic packing" Journal of the American Chemical Society 2006, 128, 7291-7298.
Reichel et al. "Synthesis and Supramolecular Characterization of a Novel Class of Glycopyranosyl-Containing Amphiphiles." J. Org. Chem. 2000 vol. 65 pp. 3357-3366.
Silva et al., "Selective differentiation of neural progenitor cells by high-epitope density nanofibers" 2004, Science 303:1352-55.
Stendahl et al., "Intermolecular Forces in the Self-Assembly of Peptide Amphiphile Nanofibers" 2006, Adv. Func. Mat. 16:499-508.
Su et al., "Biosensor signal amplification of vesicles functionalized with glycolipid for colorimetric detection of *Escherichia coli*" 2005, J. Coll. Int. Sci. 284:114-19.
Uemura, et al. "Topotactic linear radical polymerization of divinylbenzenes in porous coordination polymers" Angew Chem Int Ed Engl. 2007;46(26):4987-90.

* cited by examiner

*Primary Examiner* — Marcela M Cordero Garcia
(74) *Attorney, Agent, or Firm* — Casimir Jones, S.C.

(57) ABSTRACT

The present invention provides for self-assembling peptide amphiphiles that are capable of forming nanofibers. In particular, the present invention provides for diacetylene peptide amphiphiles that find use as scaffolds for tissue growth or for drug delivery.

5 Claims, 17 Drawing Sheets

Scheme 1: Polymerization reaction of diacetylenes when UV irradiated.

(a1)

KKLLA(K)-(COC$_8$H$_{16}$)
        -diacetylene-(C$_{12}$H$_{25}$)

(a2)

RGDSKKLLA(K)-(COC$_8$H$_{16}$)
        -diacetylene-(C$_{12}$H$_{25}$)

(b)

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: The residue at this position is linked to
      OC25H40

<400> SEQUENCE: 1

Lys Lys Leu Leu Ala Lys
1               5
```

```
<210> SEQ ID NO 2
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: The residue at this position is linked to
      OC25H40

<400> SEQUENCE: 2

Lys Lys Lys Leu Leu Ala Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic

<400> SEQUENCE: 3

Ala Ala Ala Ala Gly Gly Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: The residue at this position is linked to
      (COC8H16)-diacetylene-(C12H25)

<400> SEQUENCE: 4

Lys Lys Leu Leu Ala Lys
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: The residue at this position is linked to
      (COC8H16)-diacetylene-(C12H25)

<400> SEQUENCE: 5

Arg Gly Asp Ser Lys Lys Leu Leu Ala Lys
1               5                   10
```

SELF-ASSEMBLING PEPTIDE AMPHIPHILES

This Application claims priority to provisional patent application Ser. No. 60/857,931, filed Nov. 9, 2006, which is herein incorporated by reference in its entirety.

This application was funded by Grant No. 1R01DE015920-01A1 awarded by the National Institute of Health NIDCR and funded by Grant No. DMR0520513 awarded by the National Science Foundation. The government has certain rights in this invention.

FIELD OF THE INVENTION

The present invention provides for self-assembling peptide amphiphiles that are capable of forming nanofibers. In particular, the present invention provides for diacetylene peptide amphiphiles that are useful as scaffolds for tissue growth or for drug delivery or testing.

BACKGROUND OF THE INVENTION

There has been much interest in the development of bioactive tissue scaffolds that can be implanted into an injured area in order to enhance healthy tissue regeneration. Previous studies of bioactive peptide amphiphiles (PA) have suggested promising results as tissue scaffolds, however delivery of the scaffolds to the surgical location has been challenging due to the mechanical nature of the weak PA hydrogel.

As such, what are needed are bioactive tissue scaffolds that provide scaffolds for tissue growth that will withstand manipulation and the rigors associated with surgical implantation.

SUMMARY OF THE INVENTION

The present invention provides for self-assembling peptide amphiphiles that are capable of forming nanofibers. In particular, the present invention provides for self assembled nanofibers of diacetylene peptide amphiphiles that are useful as scaffolds for tissue growth or for drug delivery or testing.

For example, in some embodiments, the present invention provides a composition comprising a peptide amphiphile (e.g., comprising a crosslinkable or polymerizable moiety (e.g., a diacetylene) (e.g., in the alkyl tail region)) such that the peptide amphiphile is capable of forming nanofibers containing β-sheets. In some embodiments, the composition further comprises bioactive epitopes.

The present invention further provides a self assembled polymer of a peptide amphiphile (e.g., comprising a crosslinkable or polymerizable moiety (e.g., diacetylene)). In some embodiments, the polymer comprises a conjugated polydiacetylene backbone. In some embodiments, the polymer comprises cylindrical nanofibers. In some embodiments, the peptidic segment of the peptide amphiphile has a linear architecture. In some embodiments, the peptide amphiphiles further comprise bioactive epitopes. In some embodiments, the peptide amphiphile comprises a crosslinkable moiety in an alkyl tail region of the peptide amphiphile. In some embodiments, the crosslinkable or polymerizable moiety (e.g., diacetylene) is crosslinked or polymerized.

The present invention also provides a bioactive tissue scaffold comprising the polymer. The present invention additionally provides for methods of using the described compositions and polymers in drug delivery, drug screening, research and clinical uses.

Additional embodiments are described herein.

DEFINITIONS

Figure 1:
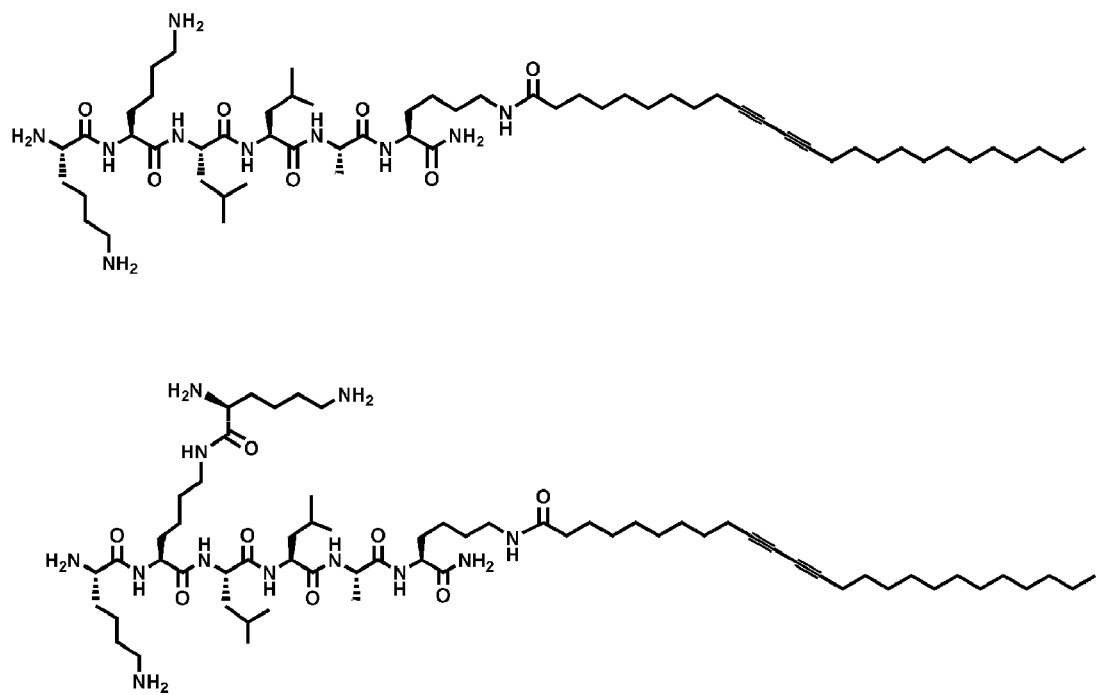
FIG. 1 depicts the general structure of the diacetylene peptide amphiphiles without the bioactive epitopes as a; A) 'linear' PA or B) 'branched' PA. The diacetylene linker is located in the alkyl tail region of the molecule. Epitope binding occurs through the primary $NH_2$ groups.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "viable cell scaffold" refers to the arrangement of the peptide amphiphiles as described herein such that cells, for example mammalian cells or tissue, can attach, grow and remain viable (e.g., survive for days, weeks, proliferate, divide, etc.) while attached to the scaffold.

As used herein, the term "crosslinkable moiety" refers to any moiety or compound that can be crosslinked (e.g., spontaneously or using chemical or environmental (e.g., heat or light) methods). Examples of crosslinkable moieties include, but are not limited to, coumarins, maleimide derivatives and divinylbenzenes.

As used herein, the term "polymerizable moiety" refers to any moiety or compound that can be polymerized (e.g., spontaneously or using chemical or environmental (e.g., heat or light) methods). Examples of polymerizable moieties include, but are not limited to, diacetylene.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present invention.

DETAILED DESCRIPTION OF THE INVENTION

I. Peptide Amphiphiles

Self-assembly of PAs by β-sheet formation of the peptide segments and hydrophobic collapse of the aliphatic chains results in one-dimensional nanofibers or networks thereof to give gels in certain conditions. This PA nanofiber system has shown potential for various applications including regenerative medicine (Silva et al., 2004, Science 303:1352), tissue engineering (Beniash et al., 2005, Acta Bio. 1:387) or chemotherapy (Bull et al., 2005, Nano Lett. 5:1) based on the epitopes displayed on the periphery. However, the PA gels created to date are weak in nature, and therefore very difficult to use as substrates for tissue growth and regeneration in vivo.

Self-assembly of PAs can be controlled by pH, electrostatic interaction, and addition of multivalent ions, causing the ionic character of certain amino acid side chains to be screened so that PAs can effectively interact with each other through hydrogen bonding and induced hydrophobic collapse (Hartgerink et al., 2002; Hartgerink et al., 2001; Niece et al., 2003, J. Am. Chem. Soc. 125:7146; Stendahl et al., 2006, Adv. Func. Mat. 16:499). Specifically, one class of PA systems that was designed to form nanofibers under acidic conditions is comprised of palmitic acid covalently linked to a f3-sheet forming peptide sequence such as AAAAGGG (SEQ ID NO:3), followed by a negatively charged peptide sequence such as FEE.

Some embodiments of the present invention provide that a crosslinking or polymerizable group added to a self-assembled system enhances the overall rigidity of an entire supramolecular structure, resulting in the formation of a more robust material. The PAs of the present invention self-assemble into micron-long nanofibers, driven primarily by hydrophobic forces and β-sheet formation. In some embodiments, an additional modification to these peptide amphiphiles is made, thereby enabling polymerizing functionality while still maintaining the monomer's ability to self-assemble into nanofibers. For example, the addition of a unsaturated hydrocarbon diacetylene ($C_4H_2$, also known as butadiyne and buta-1,3-diyne) crosslinker into the alkyl tail region of the monomer exhibits polymerization along the z-axis of the fiber. Crosslinking a self-assembled supramolecular structure while maintaining the self-assembled PA structure creates stiffer self-supporting PA hydrogels. In comparison to non-polymerized PAs that form weak gels that cannot withstand physical manipulation, the polymerized crosslinked PAs can physically be manipulated without breaking the hydrogel form. The present invention is not limited to a particular crosslinker. Other crosslinkable moieties, including coumarins or maleimide derivatives which embody similar topotactic chemistry, may be used. In other embodiments, divinylbenzenes (e.g., Angew Chem Int Ed Engl. 2007; 46(26): 4987-90) are used as crosslinking agents.

In some embodiments, the hydrogels of the present invention provide PA molecules containing diacetylene molecules with a β-sheet forming region that are able to self-assemble into high aspect-ratio nanofibers. In contrast, prior molecules were synthesized for either monolayer or LB-film studies (Nezu and Lando, 1995, 33:2455; Biesalski et al, 2005, Langmuir 21:5663; Lee et al., 2005, Nano Lett. 5:2202; Jahnke et al., 2006, Angew. Chem. 45:5383; Biesalski et al, 2006, Biomaterials 27:1259). More recent applications use the prior molecules to form crosslinked micellular nanospheres as potential biosensors or drug delivery vehicles, however none of the micellular nanospheres have proven useful to date.

The structure of a PA molecule can be divided into three major segments: i) the bioactive hydrophilic section, ii) the β-sheet forming region, and iii) the hydrophobic alkyl tail region. Self-assembly of these molecules are controlled by pH, temperature, or cation selection, depending on the peptidic sequence. Under aqueous conditions, the alkyl tails bury themselves within the interior of the fiber core, exposing the bioactive, hydrophilic segment. The morphology of the nanofiber is due to the β-sheet formation, which runs along the z-axis of the fiber. Once self-assembled, these molecules form long nanofibers which can overlap with other nanofibers to form large three-dimensional networks.

On the macroscale, the observed solution becomes a self-supporting hydrogel. The distinct regions of the PA can be tailored to accommodate various bioactive epitope sequences, while still maintaining self-assembling capabilities for hydrogel formation. The present invention is not limited by the bioactive epitope used, and any epitope that allows for the formation of three-dimensional long nanofibers as described herein may be used. Because of its flexibility, the PA of the present invention finds use as tissue regenerating scaffold material.

Current peptide amphiphiles have the mechanical consistency of a very weak hydrogel that cannot withstand significant external stress. Embodiments of the present invention provide for inclusion of a diacetylene group within the core of the alkyl tail region that serves to polymerize the nanofibers, resulting in the formation of more robust PA hydrogels. Polymerization of the nanofibers is performed by irradiation at <300 nm for several minutes, resulting in the expected colorimetric change from a colorless gel to a bluish gel. The nanofibers also form in solution at very low concentrations, as observed by a color change after UV irradiation. No chemical degradation of the peptide molecules is observed upon UV irradiation and overall nanofiber morphology is maintained.

In some embodiments, the present invention provides for nanofiber formation of self-assembling peptide amphiphiles containing diacetylene polymerizable functionality. In some embodiments, the diacetylene linker is located in the alkyl tail region of the molecule as seen in FIG. 1. However, the present invention is not limited to the location of the diacetylene linker in the alkyl tail region other than the location of the diacetylene linker is such that the resultant diacetylene PA molecule can form β-sheet secondary structures and hydrogels. In some embodiments, the PA molecules of the present invention self-assemble into high aspect-ratio nanofibers. In some embodiments, the diacetylene PA structures further contain a bioactive epitope. In some embodiments, a bioactive epitope is attached to a diacetylene PA molecule by binding to a primary amine. In some embodiments, one or more bioactive epitopes are attached to a diacetylene PA through binding to one or more primary amines. In some embodiments, the one or more bioactive epitopes are the same epitope, whereas in other embodiments the one or more bioactive epitopes are one or more different epitopes.

In one embodiment, crosslinked nanofibers of diacetylene PAs are formed by irradiation with ultraviolet light at <300 nm for at least 1, at least 2, at least 3, at least 4 minutes. In some embodiments, the crosslinked nanofibers of diacetylene PAs form hydrogels able to withstand mechanical stress to a greater extent than hydrogels formed without diacetylene.

In other embodiments, additional diacetylene contained molecules are utilized to form polymers. Examples include, but are not limited to, 5,7-docosadiynoic acid, 5,7-pentacosadiynoic acid, and 10,12-pentacosadiynoic acid (See e.g., U.S. Pat. No. 6,306,598; herein incorporated by reference).

Figure 16:
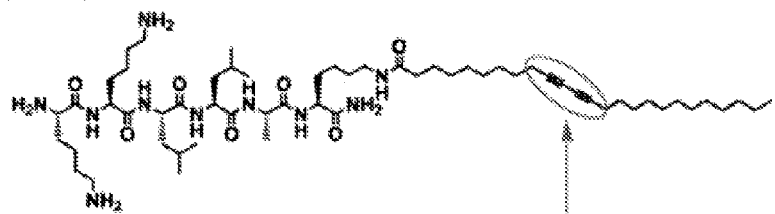
FIG. 16 shows a schematic of crosslinked PA nanofibers.
Figure 16:
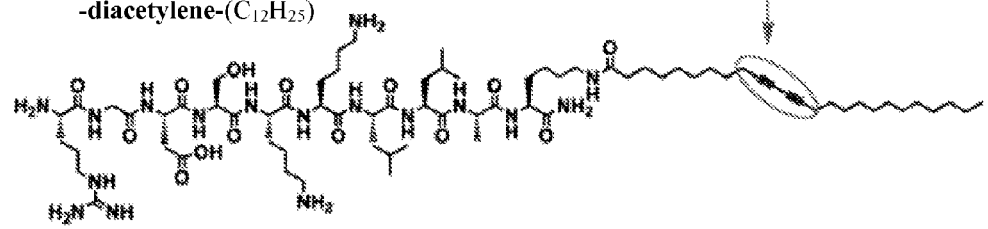
Figure 16:
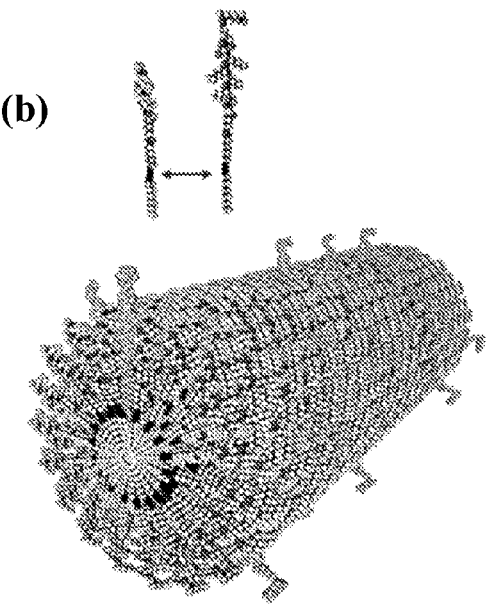

FIG. 16 shows an exemplary PA and nanofiber that finds use in some embodiments described herein. FIG. 16 illustrates the molecular structure of two individual PA molecules (a) and the corresponding self-assembled nanofiber (b). The molecular structure of both individual peptide amphiphile molecules comprises a photo-crosslinkable diacetylene segment in the hydrophobic alkyl tail of the PA to promote intra fiber crosslinks. The first PA molecule (a1) does not contain a bioactive epitope and serves as a filler to space out the bioactive PA molecule (a2), which has the amino acid sequence arginine-glycine-aspartic acid (RGD) for integrin-based recognition and subsequent improved cell adhesion (a2). (b) Illustration of the self-assembled nanofiber consisting of ~10% of the RGD-containing PA (a2) and ~90% of the filler PA (a1).

Each PA molecule comprises a diacetylene segment on the hydrophobic alkyl tail. Self-assembly of the PA molecules results from hydrophobic collapse of the aliphatic tails and β-sheet formations, which results in well defined nanofibers of about 8 nm in diameter and microns in length with the hydrophilic bioactive segment exposed at its surface. At this point, the PA nanofibers (made from assembled PA molecules) are exposed to UV light (265 nm wavelength), which leads to a polymerization reaction that results in a polydiacetylene backbone within the nanofiber.

II. Uses of Self-Assembled PAs

In some embodiments, the hydrogels are used as viable cell scaffolds. In some embodiments, the viable cells scaffolds of Pas (e.g., crosslinkable/polymerizable (e.g., via diacetylene)) PAs contain one or more bioactive epitopes. In some embodiments, the viable cell scaffolds are used in vitro to grow cells. In some embodiments, the cell scaffolds are used in vitro to grow stem cells. In some embodiments, the cell scaffolds are used in vitro to grow differentiating stem cells for implantation in vivo.

Crosslinkable biosensors are also developed that can be applied in vitro and in vivo and find use for monitoring the interactions of various molecules with the PA matrices by calorimetric changes of the matrices (Su et al., 2005, J. Coll. Int. Sci. 284:114; Kolusheva et al., 2006, J. Am. Chem. Soc. 128:13592).

In one embodiment, the hydrogels formed with diacetylene PAs, with or without bioactive epitopes, are implanted in vivo is a subject. In some embodiments, said subject is a mouse, a rat, a non-human primate, or a human. In some embodiments, the implanted hydrogel contains a bioactive epitope that will allow for attachment, differentiation, and growth of mammalian cells for treatment of trauma, disease or genetic defect. In some embodiments, the cells that attach, differentiate and grow on the hydrogels are stem cells. The present invention is not limited by the cell type used, and a skilled artisan will appreciate the myriad of cell types that could be used with the PAs as described herein. It is further contemplated that the implantation of the hydrogels as described herein also find use in drug delivery, such that cells that produce therapeutic proteins and compounds can be grown on the hydrogels which are then implanted into the affected area for localized, long term delivery of therapeutic compounds to treat diseases. In some embodiments, the hydrogels of the present invention find use in drug delivery such that drugs are impregnated into the hydrogel matrix, implanted in the affected area in a subject, thereby allowing for release of the drug from the matrix over a period of time such that localized treatment is effected. For example, a chemotherapy drug to treat a cancer can be impregnated into the hydrogel and implanted into the area of the cancer for sustained release of the chemotherapy drug. Such drug delivery would alleviate the problems associated with a whole system administration of chemotherapy drugs that is currently practiced.

The present invention further provides a kit, comprising a container, reagents and/or other components (e.g., buffers, instructions, solid surfaces, containers, software, etc.) sufficient for, necessary for, or useful for making the compositions of the present invention and/or for practicing the methods of the present invention. A container of a kit includes, but is not limited to, a box, bag, etc. that is provided a user that includes reagents and/or components for making the compositions of the present invention and/or for practicing the methods of the present invention. For example, in some embodiments a kit of the present invention comprises a box that is provided to a user that comprises peptide amphiphiles, crosslinking/polymerizing devices, and for example, additional buffers and reagents for making self assembled and crosslinked or polymerized peptide amphiphiles. In some embodiments, the kits would also include instructions for making the compositions of the present invention. In some embodiments, further instructions may include how to use the created compositions in vitro (e.g., in cell culture) or in vivo in a subject. A skilled artisan would understand the different permutations a kit of the present invention would comprise, including different storage conditions required for different components found in a kit of the present invention (e.g., storage conditions such as temperature and light requirements that differ between the different components in the kit).

In some embodiments, the present invention provides pharmaceutically acceptable compositions for use in vivo in a subject. One of skill in the art will appreciate that any one or more of the compounds described herein, including the many specific embodiments, are prepared by applying standard pharmaceutical manufacturing procedures. Such compositions can be delivered to the subject by using delivery methods that are well-known in the pharmaceutical arts. For a more detailed description of therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al, 2002, incorporated herein in its entirety.

In some embodiments of the present invention, the compositions are administered alone, while in some other embodiments, the compositions are preferably present in a pharmaceutical formulation comprising at least one active ingredient/agent, as defined above, together with one or more pharmaceutically acceptable carriers, adjuvants and optionally other therapeutic agents. Each carrier should be "acceptable" in the sense that it is compatible with the other ingredients of the formulation and not injurious to the subject.

Contemplated formulations include, for example, oral administration, parenteral administration (e.g., subcutaneous, intramuscular, intravenous, intradermal) and site specific administration. In some embodiments, formulations are conveniently presented in unit dosage form and are prepared by any method known in the art of pharmacy. Such methods include the step of bringing into association the active ingredient with the carrier that constitutes one or more accessory ingredients. In general, the formulations are prepared by uniformly and intimately bringing into association (e.g., mixing) the active ingredient with liquid carriers or finely divided solid carriers or both, and then if necessary shaping the product.

In some embodiments, in vivo administration of the compositions as described herein is effected in one dose, continuously or intermittently throughout the course of treatment. Methods of determining the most effective means and dosage of administration are well known to those of skill in the art and vary with, for example, the composition used for therapy, the target cell being treated and the subject being treated. Single or multiple administrations are carried out with the dose level and pattern being selected by the treating physician.

The present invention also includes methods involving co-administration of the compositions described herein with one or more additional active agents and/or adjuvants. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when treating cancer, the additional agent is a chemotherapeutic agent, anti-cancer agent, or radiation. Treating anti-inflammatory diseases may include the co-administration of compositions of the present invention with, for example, cox-2 inhibitors and/or other non-steroidal anti-inflammatory compositions and/or steroidal anti-inflammatory compositions known in the art.

In some embodiments, the present invention provides methods for using the compositions as described herein for screening for the efficacy of such compositions in inhibiting or decreasing, for example, apoptosis of cells and tissues when such cells and tissues are administered cancer, or other, therapies that are toxic to normal cells. In other embodiments, the present invention provides methods for screening the compositions of the present invention for use in wound healing or other applications of biological scaffolds. In some embodiments, methods for screening are conducted in in vitro systems. In other embodiments, these screens are conducted in in vivo systems. In some embodiments, methods of the present invention are performed in vivo in animal subjects and/or in vitro in cell lysates, cell and/or tissue explants, cellular extracts, or non-biological based assay systems.

EXPERIMENTAL

The following examples are provided in order to demonstrate and further illustrate certain preferred embodiments and aspects of the present invention and are not to be construed as limiting the scope thereof.

Example 1

Experimental Section

Peptide Amphiphile Synthesis. All amino acids and Rink MBHA resin were purchased from Novabiochem Corporation (San Diego, Calif.). 10,12-Pentacosadiynoic acid was purchased from Fluka and Alfa Aesar. n-Pentacosanoic acid was supplied by TCI America, Inc. All other reagents and solvents for peptide synthesis were purchased from Aldrich or Mallinckrodt and used as provided. Peptide amphiphiles were manually synthesized by Fmoc solid phase peptide synthesis. After the first attachment of a lysine residue (Fmoc-Lys(Mtt)-OH) on to the resin, the coupling of the pentacosadiynoic acid on to the $\epsilon$-amine occurred after cleaving the Mtt group with 5% TFA cocktail solution (TFA, TIPS, and water of 95:2.5:2.5) and dichloromethane. All other residues followed standard Fmoc chemistry. The PAs were cleaved from the resin using a cocktail comprised of TFA, TIPS, and water (95:2.5:2.5). Compound purity was analyzed by an analytical reverse-phase high performance liquid chromatography (RP-HPLC) on an Agilent HP 1050 system equipped with a Waters Atlantis C18 column (5 μm particle size, 150× 4.6 mm or 250×4.6 mm). Purification by RP-HPLC was done using a preparative Varian HPLC system equipped with a Waters Atlantis C18 preparative column (5 μm particle size, 250×30.0 mm). Confirmation of mass and purity included ESI (LCQ Advantage) and MALDI-TOF-MS (Voyager DE Pro). FIGS. 12-15 show spectral and chromatographic data for the peptide amphiphiles.

Polymerization. Polymerizations of self-assembled diacetylene PAs were performed by irradiating at 254 nm using a compact handheld 4-W UV lamp (UVP Model UVGL-25). Samples were prepared in aqueous solution and irradiated at approximately 3 cm from the source for 2 min in a cuvette, unless otherwise noted.

Spectroscopic Characterization. UV-V is spectroscopy was performed using a Cary 500 Spectrometer for concentration and time-dependent irradiation experiments at room temperature. A model J-715 Jasco Circular Dichroism Spectrometer was used for concentration and temperature dependent CD experiments. Before data acquisition, all samples were allowed to equilibrate at the set temperature for five minutes and averaged over of four runs.

Microscopy. AFM was performed on a DI SPM instrument using tapping mode on silicon substrates that were pre-washed using piranha cleaning solution, water, and isopropyl alcohol. Standard silicon AFM tips were purchased from Asylum Research (Santa Barbara, Calif.). Samples were prepared by drop casting 1 μL of a 0.1 wt % solution onto the substrate and allowing the solvent to evaporate in air. Samples were initially prepared as 2 wt % solutions and gelled, then irradiated and diluted as necessary. TEM was performed on a Hitachi H-8100 TEM using 200 keV accelerating voltage. Samples were prepared similarly to those described in the AFM procedure by drop casting 1 μL of 0.1 wt % PA solution in aqueous solution on to a carbon-coated copper grid (SPI Supplies; West Chester, Pa.). The samples on the grid were stained for 1-3 min in phosphotungstic acid, gently rinsed in water and blotted dry.

Results and Discussion

Figure 4:
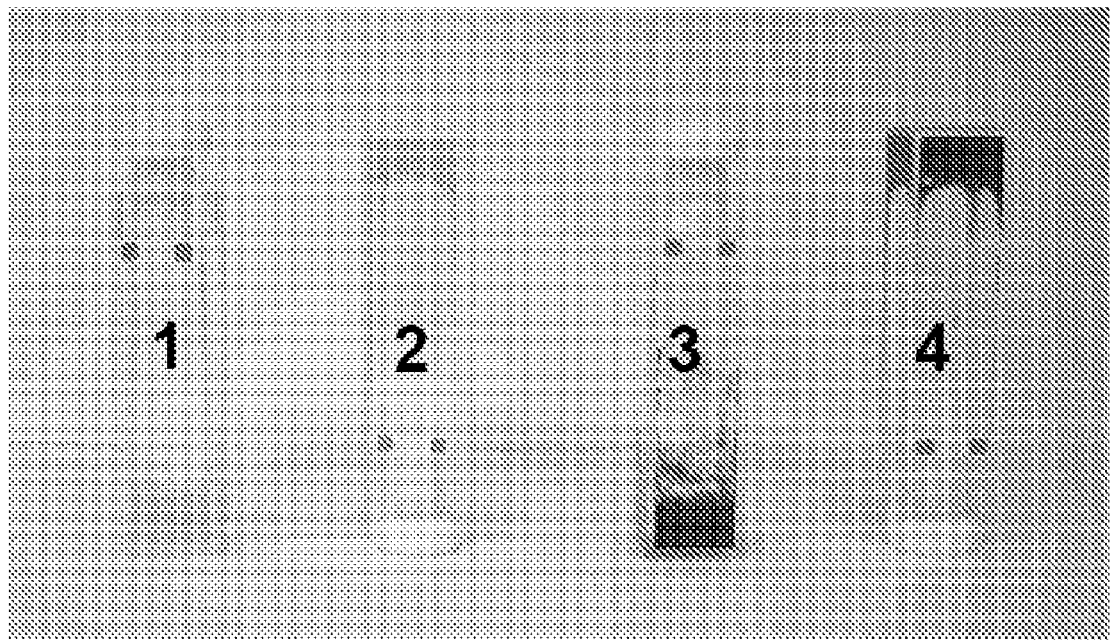
FIG. 4 shows Linear PA samples from left to right: (1) PA solution without irradiation, (2) gelled PA without irradiation, (3) PA solution with irradiation, (4) gelled PA with irradiation.
Figure 5:
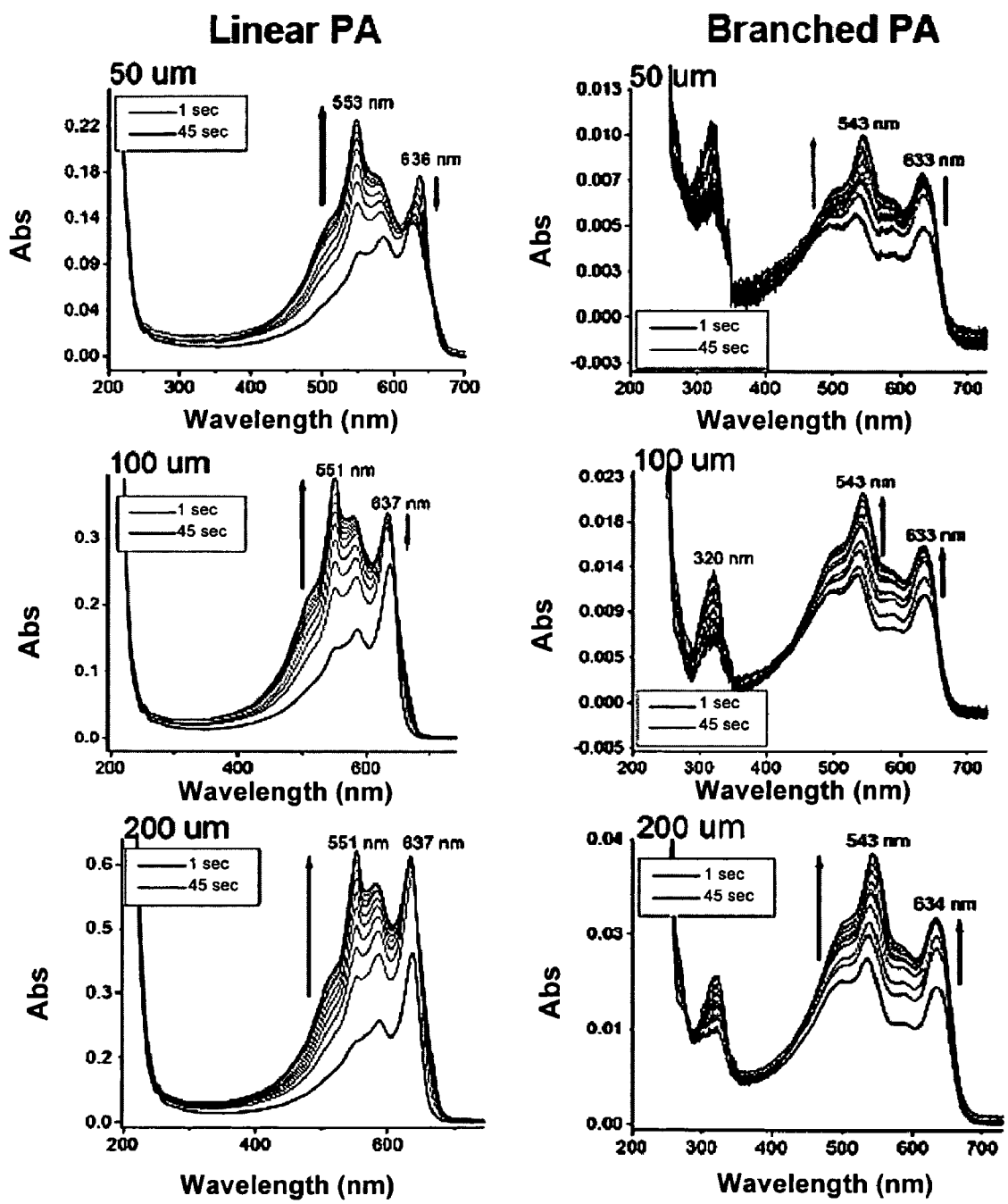
FIG. 5 shows Time-dependent UV spectroscopy of linear (left) and branched (right) PAs at varying concentrations. Samples were monitored in 5 s time-intervals for 45 s. The spectra also show data of 1 s after irradiation.

The two PAs shown in Scheme 2 (FIG. 4) containing a diacetylene moiety in the alkyl tail were synthesized. The peptide sequence of linear PA 1 has the sequence Lys-Lys- Leu-Leu-Ala-Lys(OC$_{25}$H$_{40}$) (SEQ ID NO:1) whereas PA 2 contains an additional lysine residue to create its branched architecture Lys-Lys(Lys)-Leu-Leu-Ala-Lys(OC$_{25}$H$_{40}$) (SEQ ID NO: 2).

Both linear 1 and branched 2 PAs were found to form gels at concentrations of 2.0 wt % in water when exposed to ammonium hydroxide vapor in a sealed chamber for five to ten minutes. The presence of base reduces and screens the net charges on PA molecules thus driving self-assembly into nanofibers through hydrogen bonding and hydrophobic collapse. Samples were irradiated at 256 nm either before or after gelation, both resulting in the well-known calorimetric change associated with diacetylene polymerization, from colorless to an intense blue color (see FIG. 4). Irradiated samples that had not been exposed to ammonium hydroxide vapor also polymerize after exposure to UV light, indicating that the PA aggregates exist in solution even without the base-induced gelation procedure. The irradiation of PA solutions changes color to dark purple (3 in FIG. 4), while irradiation of the gel results in an intense blue color (4 in FIG. 4). The purple color suggests the presence of both conformationally disordered (red) and ordered (blue) states in the PDA backbones formed. Irradiation of the branched PAs under the same conditions resulted in similar color changes. After polymerization, the PA gels also appeared more mechanically robust relative to nonirradiated PA gels. This change in mechanical properties is clearly due to the formation of polydiacetylene backbones within the nanofibers. It was concluded from these observations that PA nanofibers consisting of either linear or branched molecules have sufficient internal order to support the topotactic polymerization of diacetylenes in their hydrophobic core.

A blue color following diacetylene polymerization in peptide amphiphiles was observed in the low curvature planar assemblies of large vesicles (70-150 nm) by Tirrell et al. (Biesalski et al., Langmuir 2005, 21, 5663-5666). Since diacetylene polymerization is a topotactic reaction, the color change due to backbone conjugation can be correlated to the degree of molecular ordering in the reactive assemblies. This ordering should be compromised by high curvature in the assemblies and in fact the blue color indicative of long, effective conjugation length was not observed in spherical micelles by Huo et al. (Huo et al., Chemical Communications 1999, 1601-1602) and Okada et al. (Okada et al., Accounts Of Chemical Research 1998, 31, 229-239). The nanoscale cylindrical assemblies with high curvature (5-8 nm) described herein produce an intense blue color. This indicates a high degree of internal order in the cylindrical nanostructures formed by the βPAs studied here.

Spectroscopic Analysis of Nanofibers. As mentioned previously polydiacetylenes show calorimetric changes switching between blue to red when their conjugated backbone is perturbed from ordered to disordered states, respectively. UV-vis spectroscopy and circular dichroism (CD) were utilized to monitor diacetylene absorption bands after irradiation.

Figure 6:
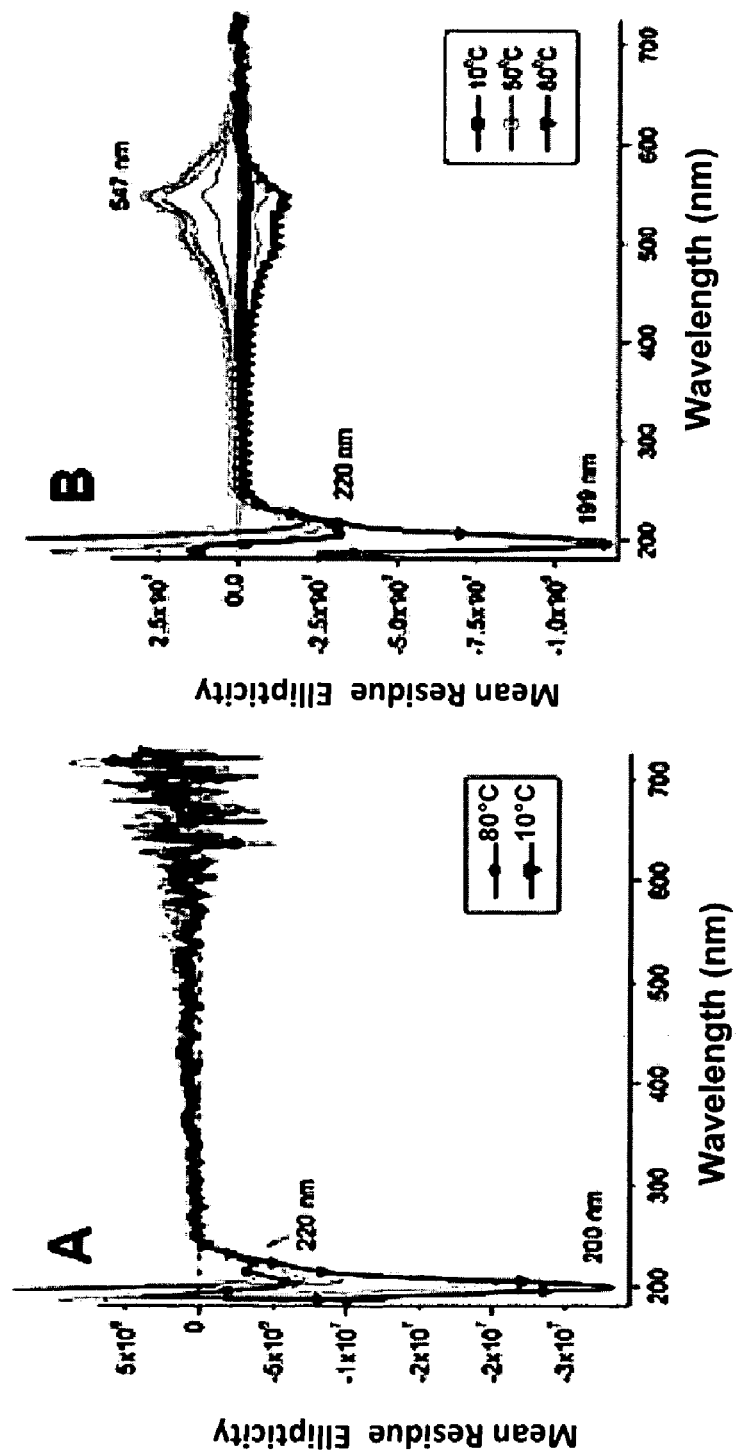
FIG. 6 shows temperature-dependent CD spectroscopy of linear PAs before (A) and after (B) irradiation. Samples were monitored from 80° C.-10° C. and irradiated for 2 minutes.
Figure 7:
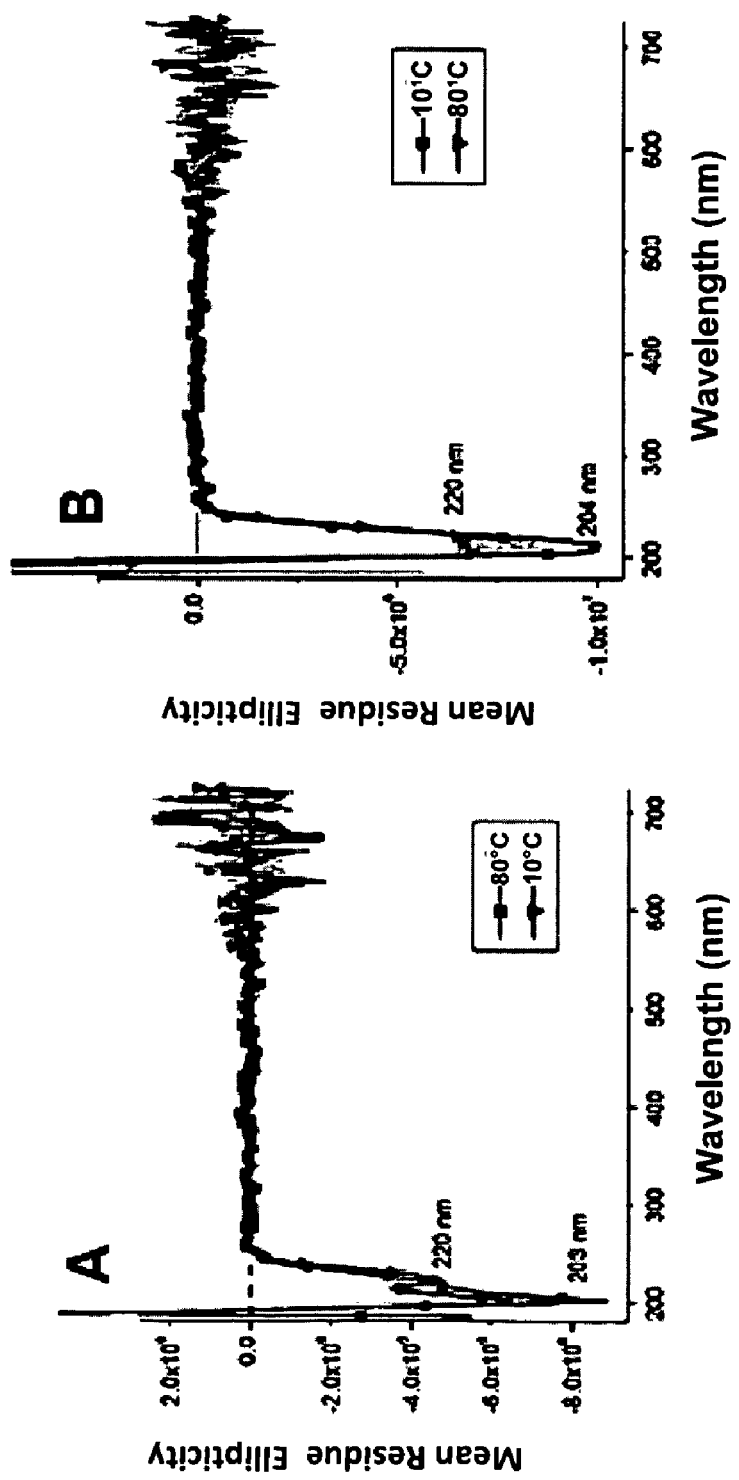
FIG. 7 shows temperature-dependent CD spectroscopy of branched PAs before (A) and after (B) irradiation. Samples were monitored from 80° C.-10° C. and irradiated for 2 minutes.

Using PA solutions diluted to concentrations of 50 μM, 100 μM, and 200 μM, UV-vis absorption was monitored for 45 seconds as shown in FIG. 6. For the spectra of both linear and branched PA samples, two major absorption peaks are observed near 530 nm (red state) and 630 nm (blue state), which are attributed to two different backbone conformational states. The band observed at 550 nm for PA 1 spectra appears to be a superposition of the 530 nm band and the band at 585 nm of the blue state (Paramonov et al., Journal of the American Chemical Society 2006, 128, 7291-7298). The presence of ordered (blue) and disordered (red) states in both the linear and branched PAs spectra is clearly revealed in the spectra obtained. After several seconds of continued irradiation, the intensity of the blue state band decreases and that of the red state band increases. Ultimately, even as samples continued to be irradiated for a total of 2 min, the rapid decrease of the band at 630 tends to be coupled with the growing band at 550 nm. The increase of the red state at 550 nm indicates that continued polymerization of the polydiacetylenes results in an increased level of disorder in the polymer backbones formed. This has been also observed in monolayers by Evans et al. (Cai et al., Langmuir 1999, 15, 1215-1222) demonstrating that extended UV exposure time decreases the effective conjugation length of polydiacetylene backbones. Similar absorption changes with irradiation were observed for PA gels that were diluted to the concentrations stated above. This UV-vis observation also indicates the PA molecules studied here under nongelating conditions exist in assembled states. Compared to the linear PA, the UV spectra of the branched PAs show significantly lower absorption. Because both are known to self-assemble into fibers, this indicates that diacetylene alkyl tails in the branched PA nanofibers are less efficiently ordered to support diacetylene polymerization. The reduced efficiency of diacetylene reaction for polymerization is the result of less efficient packing of the branched peptide segments within the nanostructure.

CD experiments were initially performed to ensure that the β-sheet structures, which help drive PA nanofiber formation, were still present after UV irradiation. The β-sheet band at 220 nm was observed both before and after irradiation, indicating that polymerization does not disrupt the hydrogen-bonded structures. Even at 80° C., the 220 nm band is still present, although markedly reduced in intensity. Random-coil bands can also be observed at 200 nm due to limited PA aggregation at the low concentration of the experiment (100 μM). The random coil band is significantly reduced in intensity at high temperatures in both spectra.

A polydiacetylene CD band was also observed at 547 nm in irradiated samples of linear PA 1, which was not expected since this portion of the molecule is not intrinsically chiral. FIG. 6 shows temperature-dependent CD spectra of non-irradiated and irradiated PA solutions at 100 μM concentrations. The signal at 547 nm was not detected in the non-irradiated sample, so it is connected with formation of the conjugated backbone in the core of the nanofibers. Further analysis of the CD spectrum (FIG. 6b) shows the PDA band changes sign starting at 80° C. from its maximum negative intensity to a maximum positive intensity at 50° C., then decreasing to a minimal intensity at 10° C. β-Sheets are known to twist naturally in helical fashion (Chothia et al., Journal of Molecular Biology 1973, 75, 295-302) and this may induce the chiral environment to the polydiacetylene backbone. Coincidentally, the preferred distance between diacetylene monomers is similar to the distance between hydrogen bonds between parallel β-sheets (~5 Å). Mori et al. have studied polymerization of diacetylene monomers using a β-sheet template and showed that the polymerization occurs parallel to the hydrogen bonds (Mori et al., Chemistry Letters 2005, 34, 116-117). The strong CD band at 547 nm from the irradiated linear PA not only shows that the PDA is in a chiral environment but suggests that β-sheets are twisted within the nanofibers. Also, the induced chiral structure of conjugated backbone is not in immediate proximity to the β-sheets, which also supports the importance of the internal order in the nanofibers.

Figure 2:
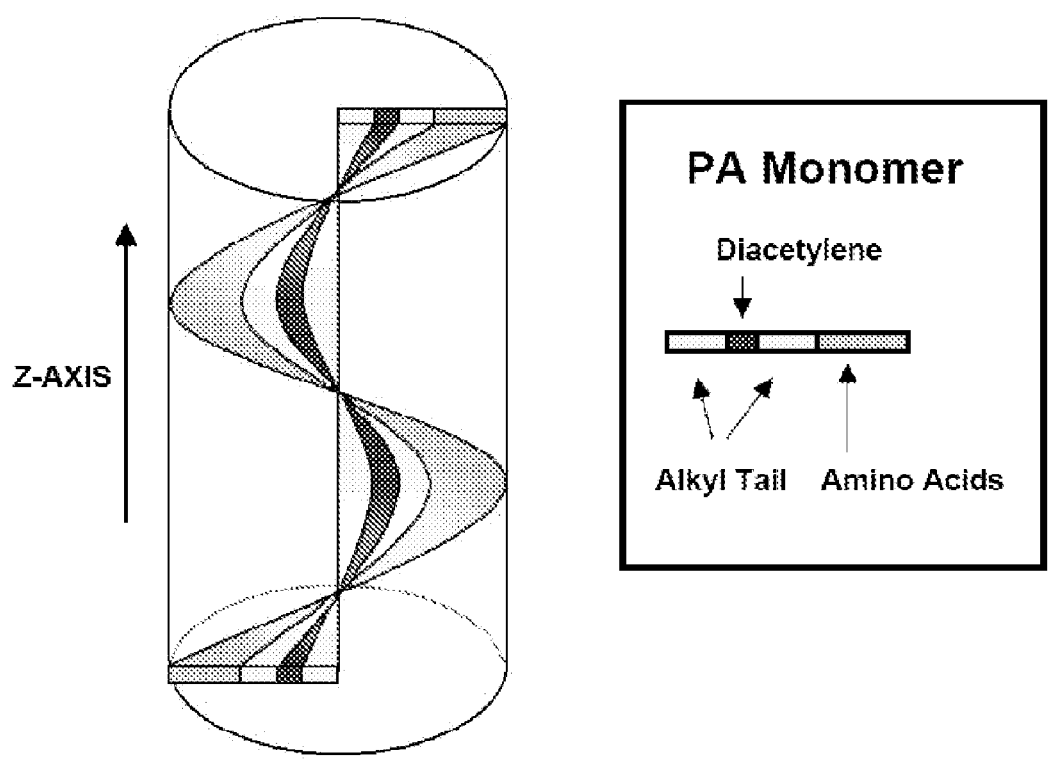
FIG. 2 shows an exemplary three-dimensional model of the PA nanofiber of some embodiments of the present invention. Polymerization of the diacetylene occurs along the z-axis of the fiber following the directionality of the β-sheet.
Figure 3:
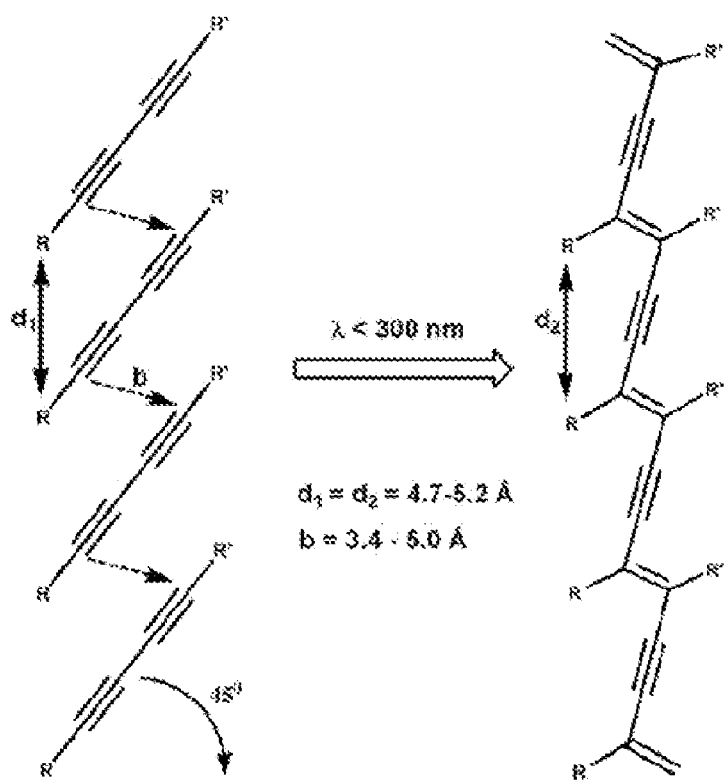
FIG. 3 shows an exemplary polymerization reaction of diacetylenes when UV irradiated.

At the same time, there is no observable CD signal for the PDA backbone in the branched PA 2. This observation, together with the low UV-Vis signal intensity from the branched PA, shows a clear structural difference between the interior core of the branched and linear PA assemblies. The packing geometry of the branched PA inhibits the polymerization reaction. FIG. 2 shows an idealized model of a polydiacetylene (red) backbone following the twisting of the β-sheet (blue).

The CD signal changes observed at 547 nm for the polymerized PA nanofibers indicates a structural relationship between the PA β-sheets and the polydiacetylene backbone. At 80° C. when the β-sheet is destabilized and partly melted, the PDA conformation appears to change (FIG. 6b) as evidenced by a change from a positive CD signal at room temperature to a negative CD signal, indicating structural reorganization within the PA assemblies involving the disappearance of nanofibers. Unlike the spectrum of the non-irradiated PA spectrum, which shows a diminished random-coil signal, the irradiated PA spectrum shows the random-coil signature from peptidic segments to be dominant at high temperatures. The continued presence of the random coil at high temperatures for the irradiated samples is due to the diacetylene polymer preventing the reorganized PA structures from completely disassembling. As the temperature decreases, the hydrogen bonds of β-sheets re-form and the PDA conformation adjusts in order to accommodate the β-sheet structure. As samples are cooled the sign of the CD signal at 547 nm also changes. The present invention is not limited to a particular mechanism. Indeed, an understanding of the mechanism is not necessary to understand the present invention. Nonetheless, the reason for this sign reversal is contemplated to be that the details of β-sheet structure (e.g., the nature of twisting) after heating the PDA-containing assemblies to 80° C. and then cooling to room temperature is different. The annealed nanofibers containing conjugated backbones are equilibrating to a new internal structure in which β-sheets and PDA backbones establish a different chiral environment. The dominance of β-sheet structure in the nanofiber assemblies at room temperature is clear as their negative CD signal signature becomes more prominent at lower temperatures. Temperature-dependent CD experiments of the branched PAs showed no significant difference before and after irradiation (FIG. 8) and, as mentioned previously, a PDA signal was not observed at 547 nm. Both β-sheet and random-coil bands at 220 nm and 200 nm, respectively, were present at high temperatures for both irradiated and nonirradiated branched PA spectra.

Figure 8:
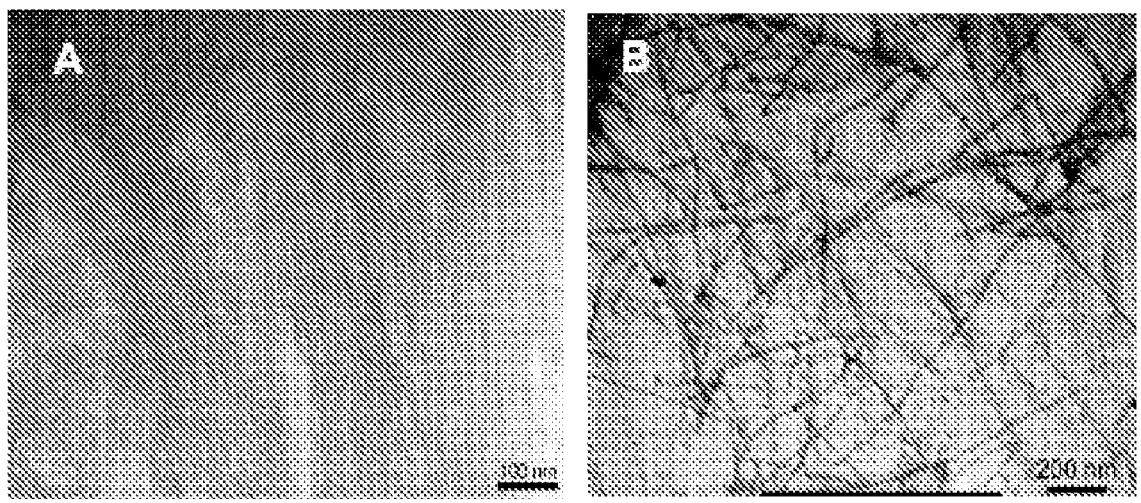
FIG. 8 shows TEM images of linear PA: nonirradiated (A) and irradiated (B). Samples were stained with phosphotungstic acid for approximately 1-3 min. Irradiated samples were exposed (256 nm) for 2 min.
Figure 9:
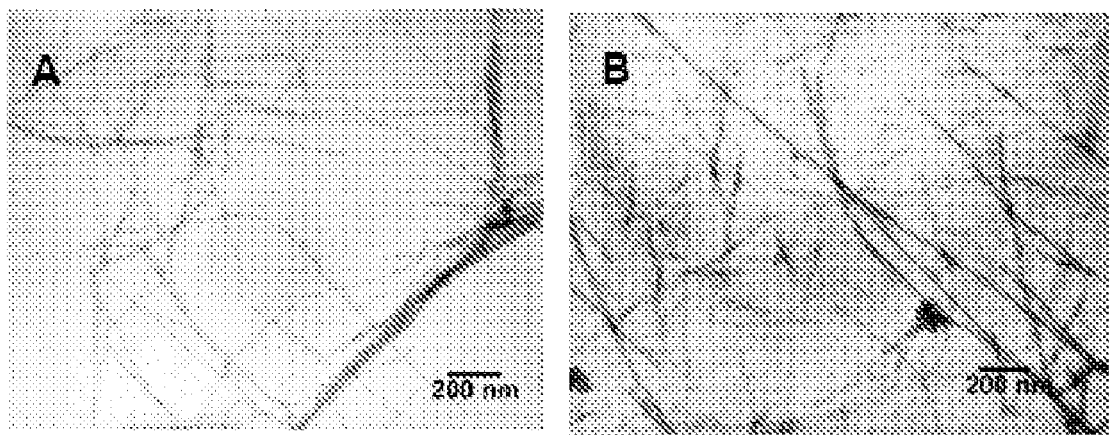
FIG. 9 shows TEM images of branched PA: nonirradiated (A) and irradiated (B). Samples were stained with phosphotungstic acid for approximately 1-3 min. Irradiated samples were exposed (256 nm) for 2 min.

Microscopic Imaging. Transmission electron microscopy (TEM) was performed on both branched and linear PAs before and after irradiation to observe morphological changes. The micrographs are shown in FIGS. 8 and 9. Both samples are clearly composed of long nanofibers with diameters in the range of 5 to 8 nm. There was no detectable change in their diameters before and after irradiation, indicating that the topochemical reaction does not alter fiber morphology. Although both formed fibers, the branched PA fibers seemed more bundled and aggregated which is explained by enhanced inter-fiber interactions as a result of less efficient packing among PA molecules within individual nanofibers.

Figure 10:
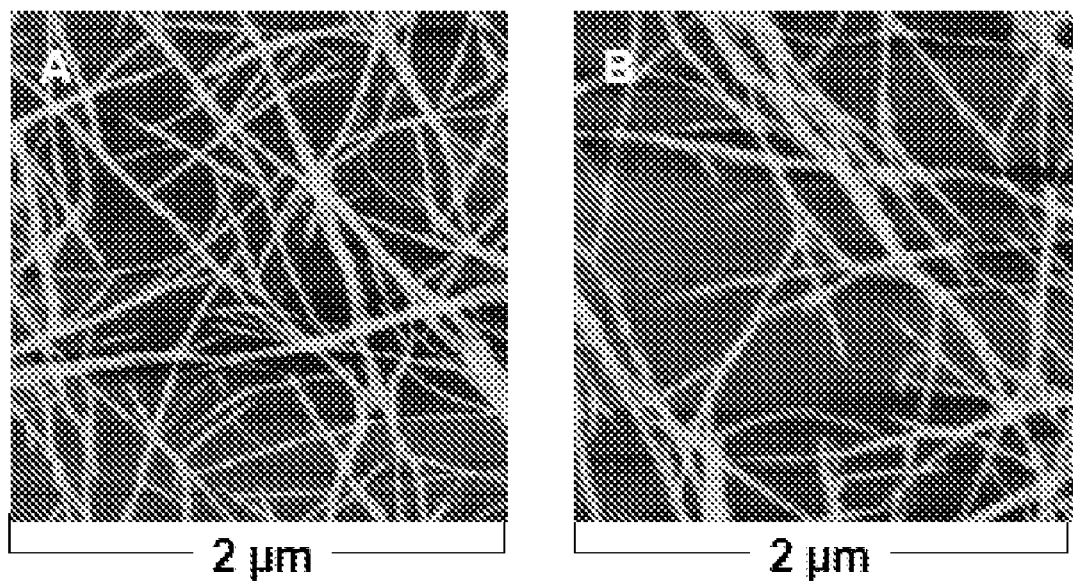
FIG. 10 shows AFM height profiles of linear PA nonirradiated (A) and irradiated (B). Samples were drop-casted and imaged on silicon substrates after 2 min of irradiation.
Figure 11:
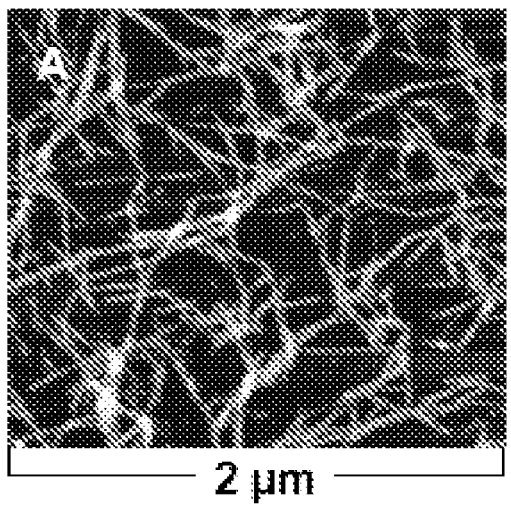
FIG. 11 shows AFM height profiles of branched PA nonirradiated (A) and irradiated (B). Samples were drop-casted and imaged on silicon substrates after 2 min of irradiation.
Figure 11:
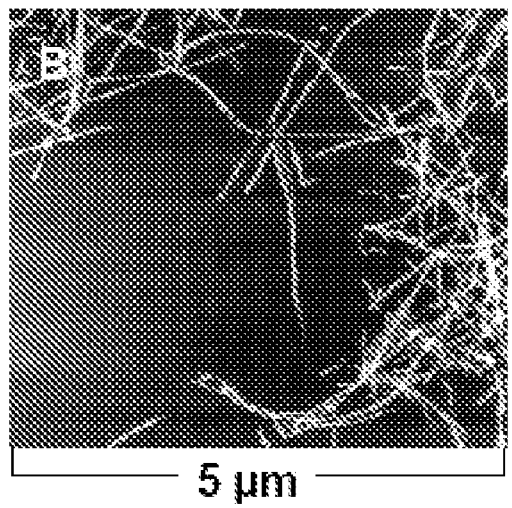
Figure 12:
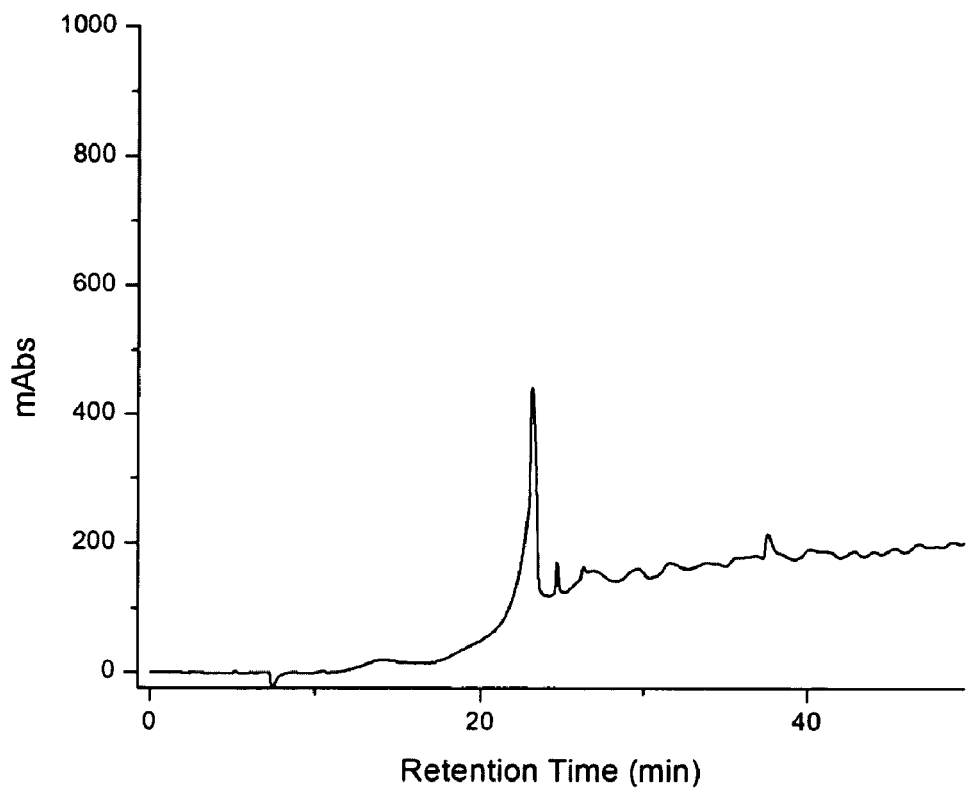
FIG. 12 shows HPLC traces of: Linear PA (A) and Branched PA (B).
Figure 12:
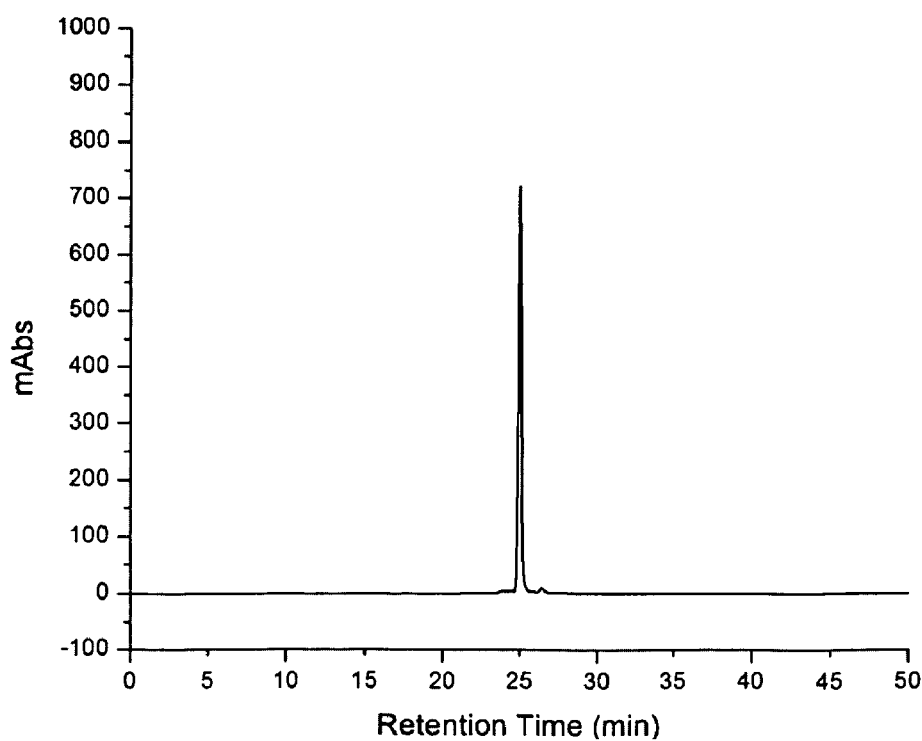
Figure 13A:
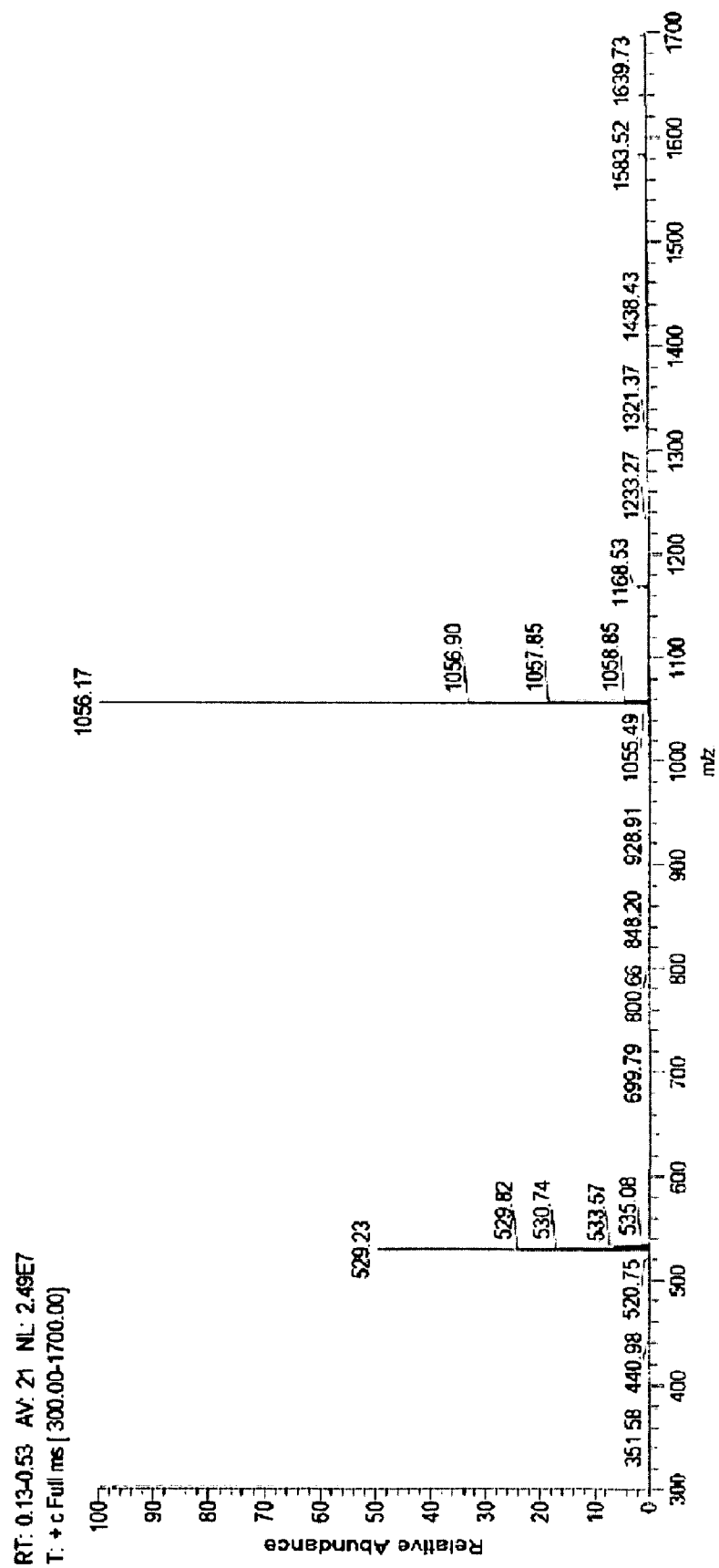
FIG. 13 shows ESI spectra of Linear PA (Top)-m/z (expected): 1055 g/mol; m/z (observed): 1056.17, m/2z (observed): 529.23. ESI spectra of Branched PA (Bottom)-m/z (expected): 1184 g/mol; m/z (observed): 1183.83, m/2z (observed): 592.93.
Figure 13B:
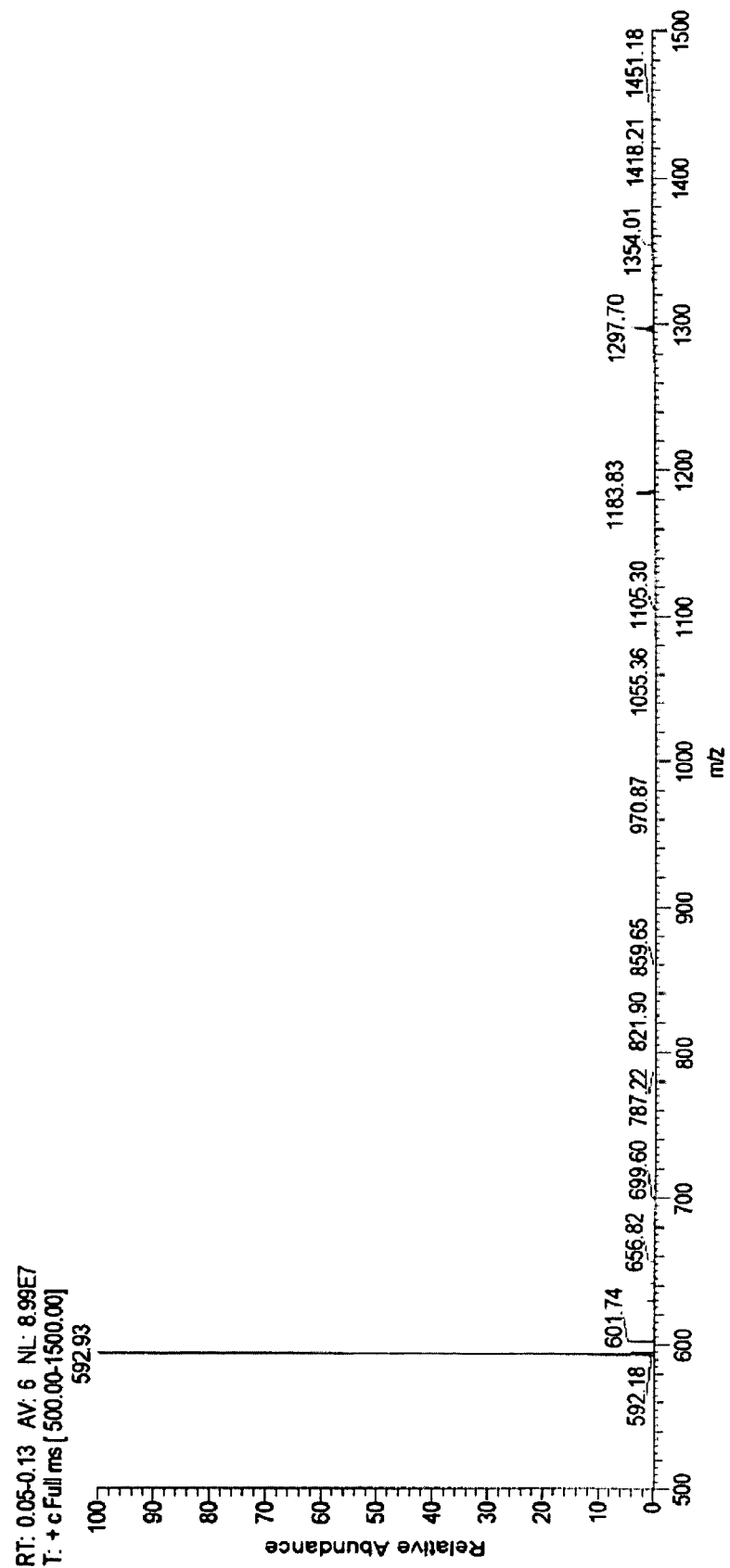
Figure 14:
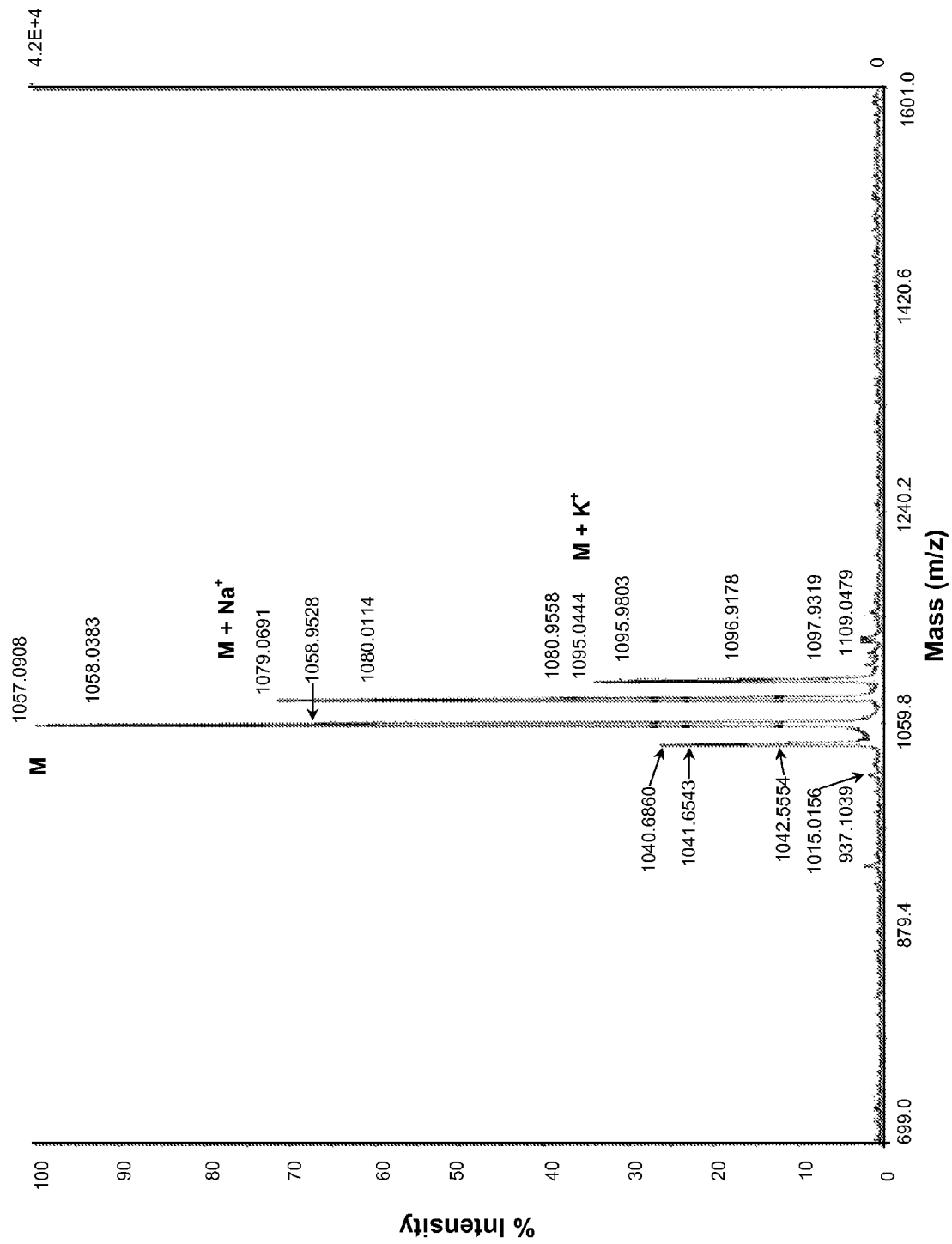
FIG. 14 shows MALDI spectrum of Linear PA-m/z (expected): 1055 g/mol; m/z (observed): 1057.
Figure 15:
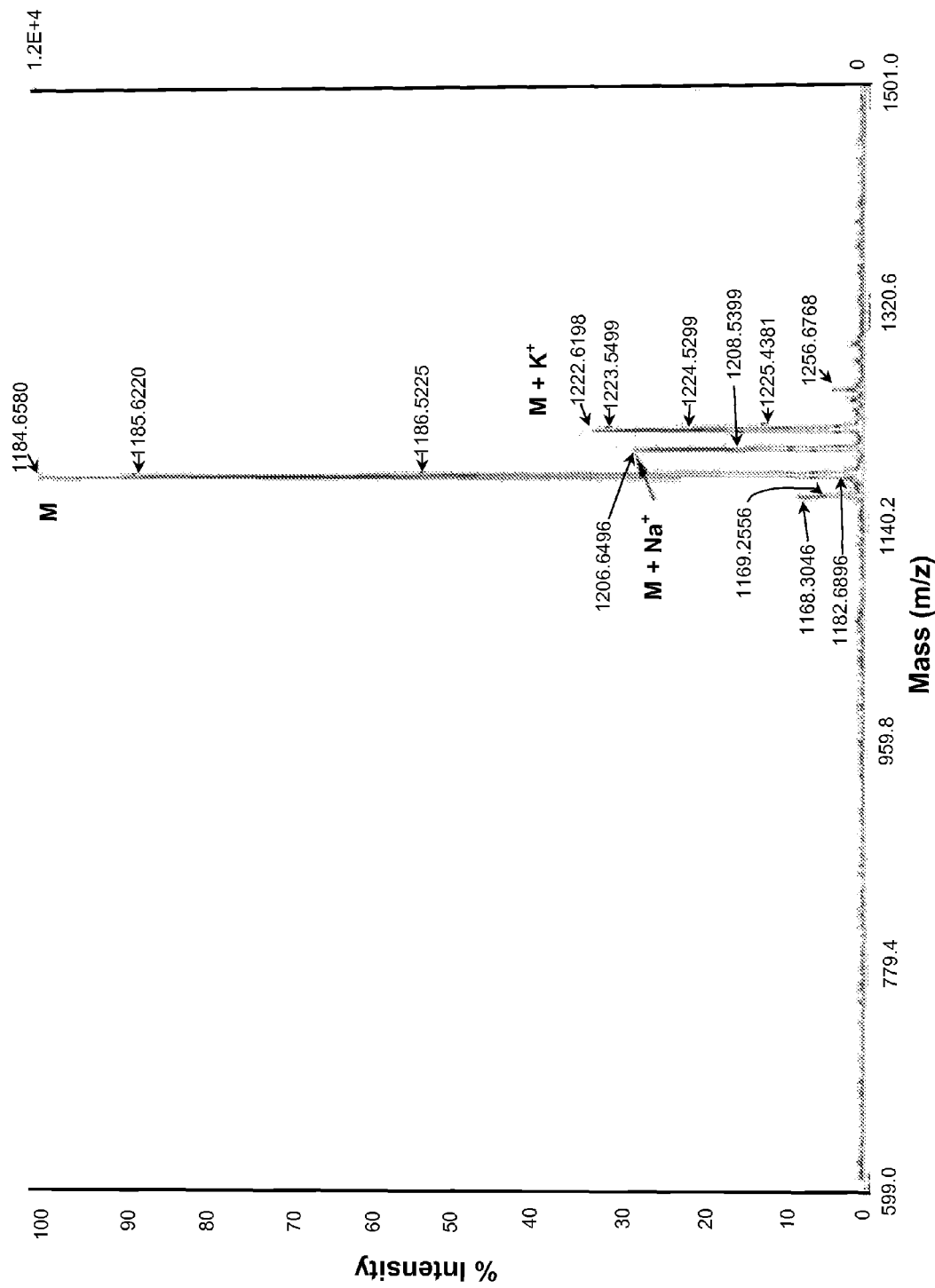
FIG. 15 shows MALDI spectrum of Branched PA-m/z (expected): 1184 g/mol; m/z (observed): 1184.66.

Atomic force microscopy (AFM) was also used to investigate the structure of samples. The AFM of linear PA samples, both irradiated and non-irradiated, revealed nanofibers with heights of approximately 5 nm and microns in length (FIG. 10). Slight undulations along the fiber were sometimes observed in the irradiated samples, due to structural defects that became trapped during the polymerization reaction giving the fiber a 'bumpy' morphology. In the samples of the branched PA samples (FIG. 11), AFM images also revealed nanofibers before and after irradiation. The fibers in this case appeared shorter with more morphology defects compared to the linear PA nanofibers.

In conclusion, this example described the polymerization of supramolecular PA nanofibers with the polydiacetylene backbone while retaining the shape of the nanostructure. The efficiency of polymerization is decreased in branched architectures due by poor molecular packing within the fiber. The β-sheet structure that is characteristic of these nanofibers is able to induce a chiral structure in the conjugated backbone, reflecting a high degree of internal order in these structures. Polymerization of these systems with conjugated backbones offers new possibilities for mechanical and optical properties, particularly in the context of biological applications.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A self assembled polymer of diacetylene-containing peptide amphiphiles comprising β-sheet-containing cylindrical nanofibers, wherein said nanofibers comprise a conjugated polydiacetylene backbone.

2. The polymer of claim 1, wherein the peptidic segment of the peptide amphiphile has a linear architecture.

3. The polymer of claim 1, further comprising bioactive epitopes.

4. The polymer of claim 1, wherein said conjugated polydiacetylene backbone is attached to an alkyl tail region of said peptide amphiphile.

5. A bioactive tissue scaffold comprising the polymer of claim 1.

* * * * *